US005843397A

United States Patent [19]

Goldenberg

[11] Patent Number: 5,843,397
[45] Date of Patent: Dec. 1, 1998

[54] CYTOTOXIC THERAPY FOR GRAFT REJECTION

[75] Inventor: Milton David Goldenberg, Short Hills, N.J.

[73] Assignee: Immunomedics, Inc., Morris Plains, N.J.

[21] Appl. No.: 803,134

[22] Filed: Feb. 18, 1997

Related U.S. Application Data

[63] Continuation of Ser. No. 412,225, Mar. 27, 1995, Pat. No. 5,609,846, which is a continuation of Ser. No. 163,408, Dec. 8, 1993, abandoned, which is a continuation of Ser. No. 876,715, Apr. 24, 1992, abandoned, which is a continuation of Ser. No. 622,188, Dec. 5, 1990, Pat. No. 5,120,525, which is a continuation of Ser. No. 174,490, Mar. 29, 1988, abandoned.

[51] Int. Cl.$^6$ .......................... A61K 51/00; A61M 36/14
[52] U.S. Cl. ......................... 424/1.41; 424/1.11; 424/9.1
[58] Field of Search .................................. 424/1.11, 1.37, 424/1.41, 1.57, 9.1, 9.2, 9.3, 9.4, 9.5, 9.6

[56] References Cited

U.S. PATENT DOCUMENTS

| | | | |
|---|---|---|---|
| 4,046,722 | 9/1977 | Rowland | 260/6 |
| 4,331,647 | 5/1982 | Goldenberg | 424/1.11 |
| 4,348,376 | 9/1982 | Goldenberg | 424/1.11 |
| 4,361,544 | 11/1982 | Goldenberg | 424/1.11 |
| 4,444,744 | 4/1984 | Goldenberg | 424/1.1 |
| 4,460,561 | 7/1984 | Goldenberg | 424/1.11 |
| 4,604,377 | 8/1986 | Fernandes et al. | 514/8 |
| 4,624,846 | 11/1986 | Goldenberg | 424/1.11 |
| 4,671,958 | 6/1987 | Rodwell et al. | 424/85 |
| 4,683,199 | 7/1987 | Palladino | 514/8 |
| 4,690,915 | 9/1987 | Rosenberg | 514/50 |
| 4,724,232 | 2/1988 | Rideout et al. | 514/50 |
| 4,734,279 | 3/1988 | Stephan et al. | 514/2 |
| 4,752,925 | 6/1988 | Martin et al. | 424/1.11 |
| 4,863,726 | 9/1989 | Stevens et al. | 514/85.2 |
| 4,894,227 | 1/1990 | Stevens et al. | 424/85.2 |
| 5,100,378 | 3/1992 | Morgan, Jr. | 604/49 |
| 5,120,525 | 6/1992 | Goldenberg | 424/1.11 |
| 5,200,176 | 4/1993 | Wong et al. | 424/85.1 |
| 5,230,886 | 7/1993 | Treon et al. | 424/85.1 |
| 5,399,338 | 3/1995 | Born et al. | 424/1.49 |
| 5,609,846 | 3/1997 | Goldenberg | 424/1.41 |

FOREIGN PATENT DOCUMENTS

| | | |
|---|---|---|
| 74521/87 | 1/1988 | Australia . |
| 76361/87 | 2/1988 | Australia . |
| 78205/87 | 3/1988 | Australia . |
| 0 256 714 | 2/1988 | European Pat. Off. . |
| 0417927 | 3/1991 | European Pat. Off. . |
| 87/03204 | 6/1987 | WIPO . |

OTHER PUBLICATIONS

Smith et al., "Increased Survival In Irradiated Animals Treated With Bacterial Endotoxins",*Am. J. Physiol,* vol. 109:124–130, (1957).

Mefferd et al., "Effect Of Piromen On Survival Of Irradiated Mice", *Proc. Soc. Exp. Biol. Med.,* vol. 83:54–63, (1953).

Ainsworth et al., "Effect Of Microbial Antigens On Irradiation Mortality In Mice", *Proc. Soc. Exp. Biol. Med.,* vol. 102:483–489, (1959).

Broudy et al., "Interleukin 1 Stimulates Human Endothelial Cells To produce Granulocyte–Macrophage Colony Stimulating Factor And Granulocyte Colony–Stimulating Factor", *J. Immunol.,* vol. 139:464–468, (1987).

Takacs et al., "IL 1 Induction By Murine T Cell Clones: Detection Of An IL 1–inducing Lymphokine" *J. Immunol.,* vol. 138:2124–2131, (1985).

Neta et al., "Interdependence Of The Radioprotective Effects Of Human Recombinant Interleukin 1 α, Fumor Necrosis Factor α, Granulocyte Colony–Stimulating Factor, And Murine Recombinant Granulocyte–Macrophage Colony–Stimulating Factor",*J. Immunol.,* vol. 140(1):108–111, (1988).

Moore et al., "Synergy Of Interleukin 1 And Granulocyte Colony–Stimulating Factor: In Vivo Stimulation Of Stem–Cell Recovery And Hematopoietic Regeneration Following 5–Fluorouracil Treatment Of Mice", *Proc. Natl. Acad. Sci., USA,* vol. 84:7134–7138, (1987).

Dinarello, (Rev. Infectious Dis.) vol. 6:51–95, (1984).

Oppenheim et al., "There Is More Than One Interleukin 1",*Immunol. Today,* vol. 7:45–56, (1986).

Farrar et al., "Participation Of Lymphocyte Activating Factor (Interleukin 1) In The Induction Of Cytotoxic T Cell Responses", *J. Immunol.,* vol. 124:1371–1377, (1980).

Mccarthy et al., "Suppression of Food Intake During Infection: Is Interleukin–1 Involved",*Am. J. Clin. Nutr.,* vol. 42:1179–1182, (1985).

Nawroth et al. "Interleukin 1 Induces Endothelial Cell Procoagulant While Suppressing Cell–Surface Anticoagulant Activity",*Proc. Natl. Acad. Sci. USA,* vol. 83:3460–3464, (1986).

Granstein et al., "In Vivo Inflammatory Activity Of Epidermal Cell–Derived Thymocyte Activating Factor And Recombinant Interleukin 1 In The Mouse", *J. Clin. Invest.,* vol.77:1020–1027, (1986).

Dukovich et al., "Stimulation of Fibroblast Proliferation And Prostaglandin Production By Purified Recombinant Murine Interleukin 1", *Clin. Immunol. Immunopathol.,* VO; 38:381–389, (1986).

(List continued on next page.)

*Primary Examiner*—Gary E. Hollinden
*Assistant Examiner*—Dameron Jones
*Attorney, Agent, or Firm*—Foley & Lardner

[57] ABSTRACT

Anticancer, antimicrobial and autoimmune disease, and anti-organ rejection therapy using cytotoxic agents is improved using cytokines to prevent, mitigate or reverse adverse radiation-induced or drug-induced toxicity, especially to hematopoietic cells. Cytotoxic agents can include radioisotopes, drugs, toxins and even unconjugated cytotoxic antibodies. A preferred cytokine is IL-1. Higher doses of cytotoxic agents can be administered and tolerated by the patient and dose-limiting marrow toxicity can be prevented, palliated or reversed using adjunct cytokine therapy.

31 Claims, No Drawings

OTHER PUBLICATIONS

Bauer et al., "Murine Interleukin 1 Stimulates $\alpha_2$ Macroglobulin Synthesis In Rat Hepatocyte Primary Cultures", *Febs Lett.*, Vol. 190(2):271–274, (1985).

Hall et al., "Stimulation of Endothelial Cell Prostacyclin Formation by Interleukin–2", *Lymphokine Res.*, vol. 5:87–96, (1986).

Tocco–Bradley et al., "The Biological Activity in Vivo of Recombinant Murine Interleukin 1 In The Rat", *Proc. Soc. Exp. Biol. Med.*, vol. 182:263–271, (1986).

Gubler et al., "Recombinant Human Interleukin 1α: Purification And Biological Characterization", *J. Immunol.*, vol. 136:2492–2497, (1986).

Kilian et al., "Interleukin 1α and Interleukin 1β Bind To The Same Receptor On T Cells", *J. Immunol.*, vol. 136(12):4509–4514, (1986).

Levine et al., "The Stimulations Of Archidonic Acid Metabolism By Recombinant Murine Interleukin 1 And Tumor Promoters Or 1–Oleoyl–2–Acetyo–Gglycerol Are Synergistic", *Jo. Immunol.*, vol. 135(5):3430–3433, (1985).

Karin et al., "Iinterleukin 1 Regulates Human Metallothionein Gene Expression", *Mol. Cell. Biol.*, vol. 5(10):2866–2869, (1985).

Ramadori et al., "Pretranslational Modulation Of Acute Phase Hepatic Protein Synthesis By Murine Recombinant Interleukin 1 (IL–1) And Purified Human IL–1", *J. Exp. Med.*, vol. 162:930–942, (1985).

Nakamura et al., *Gann*, vol. 77:1734–1739, (1986).

Nakata et al., "Augmented Antitumor Effect of Recombinant Human Interleukin–1α By Indomethacin", *Cancer Res.*, vol. 48:584–588, (1988).

Lee et al., *Experimental Hematology*, vol. 15:983–988, (1987).

Griffin, *Jour. Clin. Oncology*, vol. 7:151–155, (1989).

Perlmutter et al., "Regulation of Class III Major Histocompatibility Complex Gene Products By Interleukin–1", *Science*, vol. 232:850–852, (1986).

Gowen et al., "Actions of Recombinant Interleukin 1, Interleukin 2, and Interferon–γ oN Bone Resotrption In Vitro", *J.Immunol.*, vol. 136:2478–2482, (1986).

Woloski et al., "Corticotropin–Releasing Activity of Monolines", *Science*, vol. 230:1035–1037, (1985).

Beutler et al., "Purification Of Cachectin, A Lipoprotein Lipase–Suppressing Hormone Secreted By Endotoxin–Induced Raw 264.7 Cells", *J. Exp.. Med.*, vol. 161:984–995, (1985).

Pike et al., "Interleukin 1 Can Act As A B–Cell Growth And Differentiation Factor", *Proc. Natl. Acad. Sci. USA*, vol. 82:8153–8157, (1985).

Bussolino et al., "Interleukin 1 Stimulates Platelet–Activating Factor Production In Cultured Human Endothelial Cells", *J. Clin. Invest.*, vol. 77:2027–2033, (1986).

Lovett et al., "Macrophage Cytotoxicity: Interleukin 1 As A Mediator Of Tumor Cytostasis", *J. Immunol.*, vol. 136:340–347, (1986).

Onozaki et al., "Role Of Interleukin 1 In Promoting Human Monocyte–Mediated Tumor Cytotoxicity", *J. Immunol.*, vol. 135:314–320, (1985).

Herrmann et al., *Jour. Clin. Oncology*, vol. 7:159–167, (1989).

Brandt et al, *N. Engl. J. Med.*, vol. 318:869–876, (1988).

Gabrilove et al., *N. Engl. J. Med.*, vol. 318:1414–1422, (1988).

Boraschi et al., *J. Exp. Med.*, vol. 168:675–686, (1988).

Neta et al., *The Journal of Immunology*, vol. 136:2483–2485, (1987).

Lomedico et al., "Molecular Biology of Interleukin–1," *Cold Spring Harbor Symp. Quan. Biology*, vol. L1:631–639, (1986).

Donahue, et al., "Stimulation of Haematopoiesis In Primates By Continuous Infusion Of Recombinant Human GM–CSF", *Nature*, vol. 321:872–875, (1986).

Nienhuis et al., "Recombinant Human Granulocyte–Macrophage Colony–Stimulating Factor (GM–CSF) Shortens The Period Of Neutropenia After Autologous Bone Marrow Transplantation In A Primate Model", *J. Clin. Invest.*, vol. 80:573–577, (1987).

Vogel et al., "Induction of Colony Stimulating Factor In Vivo by Recombinant Interleukin 1α and Recombinant Tumor Necrosis Factor $\alpha^1$", *The Journal of Immunology*, vol. 138:2143–2148, (19987).

CYTOTOXIC THERAPY FOR GRAFT REJECTION

RELATED APPLICATIONS

This application is a continuation of U.S. application Ser. No. 08/412,225, filed Mar. 27, 1995 (now U.S. Pat. No. 5,609,846), which is a continuation of U.S. application Ser. No. 08/163,408, filed Dec. 8, 1993 (now abandoned), which is a continuation of U.S. application Ser. No. 07/876,715, filed Apr. 24, 1992 (now abandoned), which is a continuation of U.S. application Ser. No. 07/622,188, filed Dec. 5, 1990 (now U.S. Pat. No. 5,120,525), which is a continuation of U.S. application Ser. No. 07/174,490, filed Mar. 29, 1988 (now abandoned).

BACKGROUND OF THE INVENTION

The present invention relates to an improved method of disease therapy with cytotoxic agents, including anticancer, antimicrobial, anti-autoimmune disease and anti-organ-rejection therapy, wherein cytokines are used to prevent, mediate or reverse radiation-induced or drug-induced or antibody-induced toxicity, especially to hematopoietic cells.

Most forms of nonsurgical cancer therapy, such as external irradiation and chemotherapy, are limited in their efficacy because of toxic side effects to normal tissues and cells, because of the limited specificity of these treatment modalities for cancer cells. This limitation is also of importance when anti-cancer antibodies are used for targeting toxic agents, such as isotopes, drugs, and toxins, to cancer sites, because, as systemic agents, they also circulate to sensitive cellular compartments such as the bone marrow. In acute radiation injury, there is destruction of lymphoid and hematopoietic compartments as a major factor in the development of septicemia and subsequent death.

In the field of organ transplantation, the recipient's cellular immune response to the foreign graft is depressed with cytotoxic agents which affect the lymphoid and other parts of the hematopoietic system. Graft acceptance is limited by the tolerance of the recipient to these cytotoxic chemicals, many of which are similar to the anticancer (antiproliferative) agents. Likewise, when using cytotoxic antimicrobial agents, particularly antiviral drugs, or when using cytotoxic drugs for autoimmune disease therapy, e.g., in treatment of systemic lupus erythematosis, a serious limitation is the toxic effects to the bone marrow and the hematopoietic cells of the body.

Many different approaches have been undertaken to protect an organism from the side effects of radiation or toxic chemicals. One approach is to replace bone marrow cells after toxicity has developed. Another is to inject a chemical blocker which competes for the site of action of the toxic drug. Still another method is to give agents which affect DNA repair mechanisms such as the chemical radioprotection afforded by thiol compounds.

Neta et al. (J. Immunol. 136:2483–2485; 1986) showed that pretreatment with recombinant interleukin-1 (IL-1) protects mice in a dose-dependent manner from the lethal effects of external beam irradiation, when the IL-1 was given 20 hr before irradiation. Administering IL-1 4 hr before irradiation significantly reduced the radioprotective effects of IL-1. However, IL-1 cannot be administered too long before irradiation, because these authors also found that at 45 hr before irradiation, a drastic reduction in survival, as compared to the mice given IL-1 at 20 hr before irradiation, was achieved. Thus, this study indicated that IL-1 should be given at a critical period before lethal irradiation.

This was the first evidence that a cytokine, which acts as a differentiation-inducing and maturation-inducing agent for a variety of cells, can initiate radioprotective events in vivo when given prior to external beam irradiation. However, other kinds of immunomodulators have been reported to confer radioprotection. Numerous impure microbial components, such as lipopolysaccharide, which are now recognized to enhance hematopoietic and immune functions, were shown to have radioprotective activity more than thirty years ago (Smith et al., Am J. Physiol. 109:124–130, 1957; Mefford et al., Proc. Soc. Exp. Biol. Med. 83:54–63, 1953; Ainsworth and Chase, Proc. Soc. Exp. Biol. Med. 102:483–489, 1959).

The effects of IL-1 are mediated through the induction of colony stimulating factor (CSF) (Vogel et al., J. Immunol. 138:2143–2148, 1987), one of many hematopoietic growth factors induced by IL-1 stimulation of endothelial cells (Broudy et al., J. Immunol. 139:464–468, 1987; Lee et al., Exp. Hematol. 15:983–988, 1987; Takacs et al., J. Immunol. 138:2124–2131, 1985). However, it was shown by Neta et al. (Lymphokine Res. 5:s105, 1986; J. Immunol. 140:108–111, 1988) that human recombinant granulocyte CSF (rG-CSF) or granulocyte-macrophage CSF (GM-CSF) alone do not confer radioprotection, but do work synergistically with IL-1 to prevent radiation death in mice. Interestingly, this study also showed that mouse strains react differently to radiation and the radioprotection of IL-1, thus making extrapolation of such effects to other species, especially humans, difficult. This lack of radiation protection by the CSF's alone is in contrast to their being able to induce a recovery of neutropenia in mice treated with the anticancer drug, 5-fluorouracil (5-FU) (Moore and Warren, Proc. Natl. Acad. SCi. USA 84:7134–7138, 1987). Likewise, these authors reported that the neutropenic effects of 5-FU could be reduced by treating the mice with the cytokine 4 hr after giving the 5-FU, and that there was a synergy of IL-1 and G-CSF in acceleration of neutrophil regeneration. These studies indicate, when compared to the work of Neta et al. (cited above) for radiation protection, that different time schedules are needed for IL-1 application in drug-induced or external beam irradiation-induced myelosuppression, and that the cytokines can act differently in their ability to prevent radiation- or chemotherapy-induced myelosuppression.

Although it has been shown that an important function of IL-1 is as an immune stimulator, a plethora of other properties have been ascribed to this substance, as contained in the reviews of Dinarello (Rev. Infectious Dis. 6:51–95, 1984; Oppenheim et al., Immunology Today 7:45–56, 1986; Lomedico et al., Cold Spring Harbor Symp. Quantit. Biol. 51:631–639, 1986):

1. Stimulation of mouse thymocyte activation (Lomedico et al., Nature 312:458, 1984);
2. stimulation of human dermal fibroblast proliferation (Dukovich et al., Clin. Immunol. Immunopathol. 38:381, 1986; Gubler et al., J. Immunol., 136:2492, 1986);
3. stimulation of IL-2 production (Kilian et al., J. Immunol. 136:4509, 1986);
4. stimulation of $PGE_2$ and collagenase production by human rheumatoid synovial cells and dermal fibroblasts (Dukovich et al., Clin. Immunol. Immunopathol. 38:381, 1986; Gubler et al., J. Immunol. 136:2492, 1986);
5. stimulation of arachidonic acid metabolism in liver and smooth muscle cells (Levine and Xiao, J. Immunol. 135:3430, 1985);

6. stimulation of metallothionein gene expression in human hepatoma cells (Karin et al., Mol. Cell. Biol. 5:2866, 1985);
7. stimulation of synthesis of certain hepatic acute-phase proteins (Bauer et al., FEBS Lett. 190:271, 1985; Ramadori et al., J. Exp. Med, 162:930, 1985; Perlmutter et al., Science 232:850, 1986; Westmacott et al., Lymphokine Res. 5:87, 1986);
8. stimulation of bone resorption in vitro (Gowen and Mundy, J. Immunol. 136:2478, 1986);
9. stimulation of ACTH production in a pituitary tumor cell line (Woloski et al., Science 230: 1035, 1985);
10. cachectin-like activity (tumor necrosis factor) to suppress lipoprotein lipase activity in adipocytes (Beutler et al., J. Exp. Med. 161:984, 1985);
11. activity as B-cell growth and differentiation factor (Pike and Nossal, Proc. Natl. Acad. Sci. USA 82:8153, 1985);
12. stimulation of platelet-activating factor production in cultured endothelial cells (Bussolino et al., J. Clin INvest. 77:2027, 1986); and
13. stimulation of monocyte- or T-cell-mediated tumor cell cytotoxicity (Lovett et al, J. Immunol. 136:340–347, 1986; Onozaki et al., J. Immunol. 135: 314–320, 1985; Farrar et al., J. Immunol. 123:1371–1377, 1980).

Whereas the above listing refers to in vitro effects of IL-1, IL-1 in vivo has been shown in rodents to (1) be pyrogenic (McCarthy et al., Am. J. Clin. Nutr. 42:1179, 1985; Tocco-Bradley et al., Proc. Soc. Exp. Biol. Med. 182:263, 1986), (2) promote leukocytosis and hypozincemia (Tocco-Bradley et al., Proc. Soc. Exp. Biol. Med. 182:263, 1986), and hypoferremia (Westmacott et al., Lymphokine Res. 5:87, 1986), (3) induce a transient suppression of food intake (McCarthy et al., Am. J. Clin. Nutr. 42:1179, 1985), (4) stimulate accumulation of procoagulant activity in endothelial cells (Nawroth et al. Proc. Natl. Acad. Sci. USA 83:3460, 1986), (5) induce a local inflammatory response in the skin (Granstein et al., J. Clin. Invest. 77:1020, 1986), and (6) inhibit the growth of murine syngeneic tumors (Nakamura et al., Gann 77:1734–1739, 1986). Therefore, the demonstration that mice can be protected from lethal doses of external beam irradiation by prior administration of IL-1 (Neta et al., J. Immunol. 136:2483, 1986), alongside all these other actions, does not predict that it will be useful in humans when given during and/or after external beam irradiation, internally administered irradiation, or systemic cytotoxic chemotherapy.

Cancer therapy using anticancer cytotoxic radioisotopes and drugs is well known. It is also well known that radioisotopes, drugs, and toxins can be conjugated to antibodies or antibody fragments which specifically bind to markers which are produced by or associated with cancer cells, and that such antibody conjugates can be used to target the radioisotopes, drugs or toxins to tumor sites to enhance their therapeutic efficacy and minimize side effects. Examples of these agents and methods are reviewed in Wawrzynczak and Thorpe (in Introduction to the Cellular and Molecular Biology of Cancer, L. M. Franks and N. M. Teich, eds, Chapter 18, pp. 378–410, Oxford University Press, Oxford, 1986), in Immunoconjugates. Antibody Conjugates in Radioimaging and Therapy of Cancer (C.-W. Vogel, ed., 3–300, Oxford University Press, New York, 1987), in Dillman, R. O. (CRC Critical Reviews in Oncology/Hematology 1:357, CRC Press, Inc., 1984), in Pastan et al. (Cell 47:641, 1986), in Vitetta et al. (Science 238:1098–1104, 1987) and in Brady et al. (Int. J. Rad. Oncol. Biol. Phys. 13:1535–1544, 1987). Other examples of the use of immunoconjugates for cancer and other forms of therapy have been disclosed, inter alia, in Goldenberg, U.S. Pat. Nos. 4,331,647, 4,348,376, 4,361,544, 4,468,457, 4,444,744, 4,460,459, 4,460,561 and 4,624,846 and in related pending application U.S. Ser. No. 005,355 (hereinafter, the "Goldenberg patents"), and in Rowland, U.S. Pat. No. 4,046,722, Rodwell et al., U.S. Pat. No. 4,671,958, and Shih et al., U.S. Pat. No. 4,699,784, the disclosures of all of which are incorporated herein in their entireties by reference.

Use of cytotoxic agents, including immunoconjugates for antimicrobial, particularly antiviral, therapy, for autoimmune disease therapy, as well as for the therapy of the recipient host's rejection of foreign organ transplants, are likewise burdened by the hematopoietic side effects of these agents, thus limiting their therapeutic efficacy.

Antibodies themselves can be used as cytotoxic agents, either by virtue of their direct, e.g., complement mediated, action upon, e.g., invading microorganisms or proliferating tumor cells, or by an indirect mode, e.g., through mobilization of T-cells (e.g., killer cells), an action known as antibody-directed cellular cytotoxicity (ADCC). Such antibody cytotoxicity, denoted herein as unconjugated cytotoxic antibody therapy, can also result in compromise of elements of the hematopoietic system, and such adverse side effects can be prevented, mitigated and/or reversed with adjunctive cytokine therapy.

A need therefore continues to exist for methods of preventing, mitigating or reversing toxicity to myeloid and hematopoietic cells, which is a limiting side effect of treatment of various diseases in humans with cytotoxic agents.

OBJECTS OF THE INVENTION

One object of the present invention is to provide an improved method of cytotoxic therapy in cancer, infectious and autoimmune diseases, and organ transplantation wherein hematopoietic or myeloid toxicity produced as a side effect of exposure to a systemic cytotoxic therapy can be prevented, mitigated or reversed.

Another object of the present invention is to permit higher doses of cytotoxic agents, alone or as immunoconjugates, to be administered to and tolerated by patients without unacceptable damage to myeloid and other hematopoietic cells and resultant dangerously low white blood cell (WBC) levels.

A further object of the present invention is to provide a method of cancer therapy which will permit certain anticancer agents to be administered by routes which would otherwise be precluded because of the unacceptable level of side effects.

Upon further study of the specification and appended claims, further objects and advantages of this invention will become apparent to those skilled in the art.

SUMMARY OF THE INVENTION

These objects are achieved, in a method of therapy of disease or graft rejection, wherein a human patient suffering from a disease susceptible to treatment with a cytotoxic agent, e.g., cancer, autoimmune disease or a microbial infection, or undergoing a tissue or organ transplant, is treated with a therapeutic amount of a cytotoxic agent which also produces hematopoietic or myeloid toxicity, by the improvement which comprises administering to the patient an amount effective for substantially preventing, mitigating or reversing such hematopoietic or myeloid toxicity of a differentiation/maturation-inducing cytokine, prior to, simultaneously with or subsequent to exposure to the cytotoxic agent.

Sterile injectable preparations and kits for use in practicing the method of the invention are also provided.

DETAILED DISCUSSION

The radioprotective effect of IL-1 in certain murine strains was shown by Neta et al. for external beam irradiation by cobalt-60 gamma rays. These authors observed radioprotective activity of IL-1 in lethally irradiated mice when the cytokine was given 20 hours before irradiation, whereas giving it earlier or later did not result in a similar protection. Much radioisotope therapy is effected with beta emitters, alpha emitters and/or with the radioisotope generated in situ by neutron activation of Boron-10 atoms (resulting in alpha emission from the unstable nuclide produced by neutron absorption.) It could not be predicted that radiation damage would be produced by similar mechanisms upon exposure to such radioisotopes, nor that cytokines would serve as radioprotectors against such radioisotopes in human patients. In light of the varied physiological effects of cytokines and the limited clinical data for their use in humans, it could not be predicted whether particular cytokines might have any radioprotective effects in humans or, if so, when and how they should be administered to achieve such effects.

It could not be predicted that drug- or toxin-induced hematopoietic or myeloid toxicity would respond to cytokine treatment in humans. Moreover, the aforementioned work of Moore and Warren indicates that different time schedules are needed for IL-1 to have its protective effects in drug-induced or radiation-induced myelosuppression. Further, other growth factors, such as G-CSF and GM-CSF behave differently in radiation or drug-protection, suggesting that the myelosuppression may be different.

This previous work could not predict that simultaneous or subsequent administration of a cytokine in humans would mitigate or reverse myeloid or hematopoietic toxicity.

Cytokines, or growth factors, are hormone-like peptides produced by diverse cells and are capable of modulating the proliferation, maturation and functional activation of particular cell types. Herein, cytokines refer to a diverse array of growth factors, such as hematopoietic cell growth factors (e.g., erythropoietin, colony stimulating factors and interleukins), nervous system growth factors (e.g., glial growth factor and nerve growth factor), mostly mesenchymal growth factors (e.g., epidermal growth factor), platelet-derived growth factor, and fibroblast growth factor I, II and III, but in this invention excluding interferons.

It will be appreciated that there may be several cytokines that are involved in inducing cell differentiation and maturation, and that cytokines may have other biological functions. This also makes it difficult to predict whether a safe and restricted biological effect can be achieved in humans, such as prevention, mitigation or reversal of myelosuppression. In the case of IL-1, there may be several forms, such as IL-1-alpha and IL-1-beta, which nevertheless appear to have a similar spectrum of biological activity. Preferred cytokines for use in the method and compositions of the invention are lymphokines, i.e., those cytokines which are primarily associated with induction of cell differentiation and maturation of myeloid and possibly other hematopoietic cells. A preferred lymphokine is IL-1. Other such lymphokines include, but are not limited to, G-CSF, M-CSF, GM-CSF, Multi-CSF (IL-3), and IL-2 (T-cell growth factor, TCGF). IL-1 appears to have its effect mostly on myeloid cells, IL-2 affects mostly T-cells, IL-3 affects mutiple precursor lymphocytes, G-CSF affects mostly granulocytes and myeloid cells, M-CSF affects mostly macrophage cells, GM-CSF affects both granulocytes and macrophage. Other growth factors affect immature platelet (thrombocyte) cells, erythroid cells, and the like.

The cytokines can be used alone or in combination to protect against, mitigate and/or reverse myeloid or hematopoietic toxicity associated with cytotoxic agents. Examples of possible combinations include IL-1+GC-CSF, IL-1+IL-3, G-CSF+IL-3, IL-1+platelet growth factor and the like. Certain combinations will be preferred, depending on the maturation state of the target cells to be affected, and the time in the course of cytotoxic action that the protective agent needs to be administered. For example, in patients with depression of several hematopoietic cell types (e.g., myeloid, lymphoid and platelet), a combination of IL-1+IL-3/and/or platelet growth factor is preferred, while more severe depression of the myeloid series may require such combinations as IL-1+ G-CSF. Certain cytotoxic agents have greater compromising effects on particular hematopoietic elements, either because of the nature of the agent or the dosage necessary to achieve a therapeutic effect, and the appropriate choice, dosage and mode of administration of cytokine(s) will follow from such effects.

Additionally, the cytokines can be used in combination with other compounds or techniques for preventing, mitigating or reversing the side effects of cytotoxic agents. Examples of such combinations include, e.g., administration of IL-1 together with a second antibody for rapid clearance, as described, e.g., in Goldenberg, U.S. Pat. No. 4,624,846, from 3 to 72 hours after administration of a targeted primary antibody or antibody fragment conjugate (with a radioisotope, drug or toxin as the cytotoxic component of the immunoconjugate) or of a non-conjugated drug or toxin, to enhance clearance of the conjugate, drug or toxin from the circulation and to mitigate or reverse myeloid and other hematopoietic toxicity caused by the therapeutic agent.

In another aspect, cancer therapy often involves a combination of more than one tumoricidal agent. e.g., a drug and a radioisotope, or a radioisotope and a Boron-10 agent for neutron-activated therapy, or a drug and a biological response modifier, or an antibody conjugate and a biological response modifier. The cytokine can be integrated into such a therapeutic regimen to maximize the efficacy of each component thereof.

Similarly, certain antileukemic and antilymphoma antibodies conjugated with radioisotopes that are beta or alpha emitters can induce myeloid and other hematopoietic side effects when these agents are not solely directed to the tumor cells, particularly when the tumor cells are in the circulation and in the blood-forming organs. Concomitant and/or subsequent administration of the cytokine is preferred to reduce or ameliorate the hematopoietic side effects, while augmenting the anticancer effects.

In addition to preventing, mitigating or reversing the myelosuppressive or other hematopoietic side effects of the therapy, cytokines such as, e.g., IL-1, can have anticancer effects (Nakamura et al., Gann 77:1734–1739, 1986; Nakata et al., Cancer Res. 48:584–588, 1988), and therefore are capable of enhancing the therapeutic effect of the targeted agents when used in combination with these other therapeutic modalities. Thus, another aspect of the present invention is to maximize the antiproliferative activity of the cytokine by conjugating it to the targeting antibody to form a heteroconjugate. Since the cytokines are polypeptides, conjugation to the antibody can be performed using any of the conventional methods for linking polypeptides to antibodies. These include, e.g., use of the heterobifunctional reagent N-succinimidyl 3-(2-pyridyldithio)propionate (SPDP), according to published procedures, e.g., that of Carlsson et al., Biochem. J. 173:723–737, 1978, use of glutaraldehyde, carbodiimide or like condensing and/or linking reagents.

It is preferable to achieve a high ratio of the cytokine to the antibody without affecting the latter's immunoreactivity and targeting properties. Thus, it may be advantageous to use a carrier for the cytokine and to link a plurality of cytokine molecules to the carrier, which is then linked to the antibody. A particularly effective method for achieving this result is to use the method of Shih et al., PCT/U.S. application Ser. No. 87/00406, wherein an addend is conjugated to a polymer such as an aminodextran, which is then site-specifically linked to the oxidized carbohydrate portion of an antibody. Depending upon the cytokine and antibody used, 20 to more than 100 cytokine molecules per immunoglobulin molecule can be attached without affecting the antibody appreciably, and in some circumstances 100 to 1,000 molecules of cytokine per antibody molecule can be achieved.

Use of IL-1 as the cytokine in this conjugate is preferable if a cytokine with antitumor activity is desired to potentiate the targeting antibody's effects, especially if the latter is conjugated with a toxic radioisotope or drug. If the targeting antibody circulates and deposits in other normal organs, such as the bone marrow, then the presence of the cytokine is important to prevent, mitigate or reverse the hematologic side effects that would normally result. Since some of the cytokines have lymphoid effector cell functions for tumor cell- killing (e.g., IL-2), the heteroconjugate of this invention provides a multimodal therapy to the target, whether it be a cancer, an infection, or another lesion that is unresponsive to more traditional measures.

As mentioned, depending upon the circumstances, an appropriate dose of the cytokine can be administered prior to, simultaneously with or subsequent to the administration of the therapeutic agent. The object will be to maximize the cytotoxic activity of the agent on the pathological lesion, such as cancer cells or infectious organisms, while minimizing toxicity to the myeloid and other hematopoietic cells. Careful monitoring of the WBC and other blood elements, including but not limited to erythrocyte (red blood cell/ RBC) count, thrombocyte (platelet) count, and including a differential WBC analysis to monitor the myloid/lymphoid series, as well as the bone marrow hematological picture during the course of therapy, with particular attention to possible depletion of myeloid lymphoid forms, but also the status of immature erythrocytes, myelocytes, lymphocytes and thrombocytes, will permit optimization of the cytokine treatment. Depending upon which hematologic element is adversely affected, the choice of cytokine and administration schedule can be individualized in each circumstance, including the combination of cytokines, such as IL-1+IL-3, Il-1+ IL-2, IL-1+GM-CSF, IL-1+platelet growth factor and the like.

Correlation of the choice of cytokine, singly or in combinations, and doses thereof, to hematotoxicity is important, since each cytokine generally has its effect mostly on particular hematopoietic elements. For example, if a cytotoxic agent has both severe myeloid and thrombocytic toxicity, the combination of IL-1 and IL-3 in a 1:1 or 2:1 (or higher) ratio will be advantageous. Thus, reduction in the WBC count to a level below about 2,000 and platelets to a level below about 20,000 can be reversed by administration of from about 1 ug to about 500 ug, preferably 5–100 ug, more preferably about 10 ug of rIL-1 in a single dose, together with or followed by administration of from about 1 ug to about 200 ug, preferably 5–50 ug, more preferaby about 5 ug of IL-3. The applications can be repeated, with the reversal of the myeloid and platelet depressions occurring within about 5–20 days, usually about 7 days. The ordinary skilled clinician will appreciate that variations in the timing and dosage of cytokine administration and cytokine combinations and dosages are a function of the cytokine used, the nature of the bone marrow and/or other hematopoietic element depressed, and the nature of the patient (e.g., prior toxicity affecting bone marrow status) and the cytotoxic agent and protocol.

The method of this invention is particularly useful for the treatment of bone pain in patients with bone metastases and primary bone cancers. In such cases, radionuclide therapy has been found to be effective and safe, particularly with the introduction of Sr-89, Y-90 and Re-186 or Re-188, either alone or conjugated to an antibody or a bone-seeking chemical such as orthophosphate or diphosphonate. Chemotherapeutic agents, e.g., 5-fluorouracil (5-FU), have also been known to control bone pain in patients with metastatic carcinoma. P-32-orthophosphate can be administered in several ways, including single doses of about 3 to 10 mCi, multiple consecutive doses of about 1.5 mCi, or multiple intermittent doses of 7 to 10 mCi as clinically required. In multiple and intermittent dose schedules, total doses can range from 5 to 20 mCi, depending on patient response and side effects. In order to reduce the myelosuppression of this treatment and encrease the effects against bone pain and possibly also inhibit tumor growth, these doses can be increased by from about 10% to about 35%, preferably 15 to 25%, by simultaneous administration of continuous or intermittent doses of about 5 to 20 ug of IL-1, more preferably single repeated doses of 5–10 ug IL-1, extending to several days post-radionuclide therapy. Similarly, Re-186-diphosphonates can be used for bone pain palliation in single doses of about 5 to 10 mCi, repeated up to three times, under simultaneous and post-therapy administration of IL-1 (5–10 ug) alone or in combination with IL-3 (2–10 ug), repeated several times during a 1–2 week therapy course.

I-131 is an effective radioisotope for treatment of primary and metastatic, well-differentiated thyroid carcinomas. A dose of 150 mCi I-131 has been successful, with most clinicians administering a dose between 100 and 200 mCi. Bone marrow depression is one of the major complications, and limits the dose tolerated by the patient. By combining I-131 therapy, using a dose of 150–250 mCi, with IL-1 (at a twice weekly dose of 5–50 ug, preferably 10 ug each, continued to 2 weeks post-therapy, myelosuppression is markedly prevented and the higher I-131 doses are well tolerated. If IL-1 therapy is instituted 1–2 days before I-131 administration, and continued twice weekly for 2–3 weeks, doses of I-131 between 200 and 300 mCi, preferably 200–250 mCi, can be well tolerated, thus increasing the therapeutic anti-cancer dose.

It is well known in the art that various methods of radionuclide therapy can be used for the treatment of cancer and other pathological conditions, as described, e.g., in Harbert, "Nuclear Medicine Therapy", New York, Thieme Medical Publishers, 1987, pp. 1–340. A clinician experienced in these procedures will readily be able to adapt the cytokine adjuvant therapy described herein to such procedures to mitigate the hematopoietic side effects thereof. Similarly, therapy with cytotoxic drugs, either administered alone or as antibody conjugates for more precisely targeted therapy, e.g., for treatment of cancer, infectious or autoimmune diseases, and for organ rejection therapy, is governed by analogous principles to radioisotope therapy with isotopes or radiolabeled antibodies. Thus, the ordinary skilled clinician will be able to adapt the description of cytokine use to mitigate marrow suppression and other such hepatopoietic side effects by administration of the cytokine before, during and/or after drug therapy.

It is also well known that invading microorganisms and proliferating cancer cells can be targeted with antibodies that bind specifically to antigens produced by or associated therewith. Such antibodies can directly induce a cytotoxic immune response, e.g., mediated by complement, or an indirect cytotoxic immune response, e.g., through stimulation and mobilization of T-cells, e.g., killer cells (ADCC). Certain of such antibodies also produce side effects which include compromise of elements of the hematopoietic system, and such side effects can be prevented, mitigated and/or reversed by cytokine therapy. Dosimetry and choice of cytokines will again be correlated to WBC, erythrocyte and platelet counts and other aspects of the status of the hematopoietic system, for which guidelines are provided herein.

The mode of administration of the therapeutic agent as well as of the cytokine should be coordinated and optimized. For example, intracavitary, e.g., intraperitoneal, administration of a radioisotope-antibody conjugate will eventually result in lowering of the WBC count in a patient given a high dose of the cytotoxic immunoconjugate, due to eventual diffusion of the conjugate into the bloodstream and circulation through the bone marrow. Administration of the cytokine is advantageously effected intravenously to have its maximum effect on the circulation through the bone marrow. Other forms of administration of the cytokine, e.g., intraarterial, intrathecal, may be advantageous for more immediate access to the region of greatest hematopoietic cell compromise.

A further parameter to consider is whether the cytokine is administered in a single dose, in multiple doses or as a continuous infusion during the course of therapy. Certain cytokines are cleared rapidly from the body and will require periodic or continuous administration in order for their efficacy to be maximized. Depending if a pre-treatment, intra-treatment, or post-treatment of the cytokine is given, the manner of administration can differ. For example, if the cytokine is given concomitantly with the cytotoxic agent, it is preferable to administer the cytokine by continuous intravenous infusion over several hours and optionally repeated on one or more days during and after completion of the cytotoxic therapy. It should also be understood that continuous administration of a cytokine can be effected by any of the transdermal modes of drug administration known to the art or vet to be developed.

Radioisotopes are administered by a variety of routes for cancer therapy. These include, e.g., intravenous, intraarterial, intracavitary (including intraperitoneal), intrathecal and subcutaneous injection, as well as by implantation of seeds of radioactive material at selected sites in the patient's body. The type, extent and time frame for myeloid and other hematopoietic cell toxicity will vary for each mode of administration of the cytotoxic agent and with the type of agent itself. In general, bone marrow toxicity will be the most serious side effect of such therapeutic regimens and intravenous or intraarterial administration of the cytokine will be the most effective preventive or palliative measure.

Similar conditions exist for the application of anticancer and antimicrobial, e.g., antiviral, drugs, whose major side effects are hematologic toxicity. These drugs, including toxins, can be administered systemically without conjugation to a tumor-targeting or infectious lesion-targeting antibody. Marrow toxicity is a common limiting factor in the dosage which can be administered, and the method of the invention is effective in significantly extending the dosage range of such agents.

Conjugation of the drugs or toxins to antibodies to achieve better targeting of the drug to the pathological lesion improves the therapeutic index. Still further improvement can be achieved by combining the immunoconjugate with cytokine administration. In some cases, drug or toxin activity is lost by attempts to conjugate the drug or toxin to an antibody, and the targeting thereby afforded is not possible. In such instances, the cytokine treatment according to the invention is a preferred method for increasing the patient's tolerance for the higher levels of drug, toxin, or other cytotoxic agent necessary for maximal therapeutic activity.

Radioisotope antibody conjugates can be administered by, e.g., intravenous, intraarterial, intracavitary, intrathecal, intramuscular, or subcutaneous routes. Again, intravenous or intraarterial administrations of cytokines will normally minimize bone marrow toxicity.

Beta and alpha emitters are preferred for radioimmunotherapy, since the patient can be treated in multiple doses on an outpatient basis. To the extent that the treatment results in bone marrow toxicity, administration of cytokines can be effected at convenient times by injection or even by transdermal administration of an appropriate level of cytokine.

Particular mention should be made of the utility of the present method for preventing and/or ameliorating marrow toxicity, the major limiting side effect of neutron activated anticancer therapy using Boron-10 compounds, as described in the aforementioned Goldenberg patents and in Hawthorne, U.S. patent application Ser. No. 742,436. Systemic administration of Boron-10-containing compounds, e.g., borates, carborane compounds and the like, followed by neutron irradiation, has been used in anticancer therapy. However, excessive toxicity to normal organs has been an unacceptable side effect of such treatments and they have not generally been very successful. Later improvements in such a therapeutic modality by conjugation of, e.g., carboranes, to anticancer antibodies, have attempted to minimize these side effects by targeting the boron atoms to tumor sites. While this therapeutic approach shows great promise, a further improvement in therapeutic efficacy is achieved by combining this treatment with a radioprotective treatment against the alpha radiation of the activated boron atoms using cytokines, according to the present invention. For example, a thermal neutron beam need not be so accurately directed to the lesion to be treated, since more generalized toxicity may be desired to destroy a larger tumor area which includes normal structures, with concomitant side effects. Use of simultaneous or post-treatment cytokine therapy to prevent or reverse hematopoietic toxicity improves the targeted cytotoxic neutron capture therapy.

Another major application of cytotoxic agents, particularly those that affect the lymphoid system (and therein particularly the T-lymphocytes), is to depress host immunity in certain autoimmune diseases, e.g., systemic lupus erythematosis, and in patients receiving organ transplants. These cytotoxic drugs are similar to those often used in cancer chemotherapy, with the attendant myeloid and other hematopoietic side effects. In addition to these drugs, specific antibodies against these lymphoid cells (particularly T-cells), e.g., the anti-Tac monoclonal antibody of Uchiyama et al., J. Immunol. 126:1393 and 1398 (1981), which specifically binds to the human IL-2 receptor of activated T-cells, can be conjugated to cytotoxic agents, such as drugs, toxins or radioisotopes, to effect a relatively select killing of these cells involved in organ rejection. For example, a T-cell antibody can be conjugated with a beta- or alpha-emitting radioisotope, and this can be administered to the patient prior to undertaking organ transplantation and, if needed, also thereafter.

In order to effect a high T-cell killing dose without the concomitant limiting side effects to the hematopoietic system, this treatment can be combined with the use of cytokines, according to the present invention. This method is preferred for the long-term survival of many organ transplants, such as the kidney, heart, liver, etc., where a critical period of organ rejection needs to be overcome.

The dosage level of the cytokine will be a function of the extent of compromise of the hematopoietic cells, correlated generally with the WBC level in the patient. Periodic monitoring of the WBC and other blood cell counts and adjustment of the rate and frequency of infusion or the dosage of the cytokine administered to achieve a relatively constant level of WBC's will ensure that the patient does not sustain undue marrow toxicity from the therapy. Experience will permit anticipation of WBC lowering and infusion of the cytokine at a time and in an amount sufficient to substantially prevent WBC depression. Importantly, this also insures that excessive side effects due to the cytokine itself are not produced, but only such side effects as are necessary to prevent compromise of the patient's myeloid and other hematopoietic cell systems.

Correlation of cytokine dosage to WBC count suggests that, in general, reduction of WBC count from a normal range of 8–12,000/cmm to a level of about 2,000 can be reversed by administration of from about 1 ug to about 500 ug, preferably 5–100 ug, more preferably about 10 ug of recombinant human IL-1 in a single dose, the reversal of WBC count depression occurring within about 2–12 days, usually about 4 days. The clinician will appreciate that variations in the timing and dosage of cytokine administration as a function of the type of cytokine used, the extent and rate of compromise of the bone marrow and/or other components of the myeloid and/or other hematopoietic elements and the individual characteristics of the patient and the therapy protocol will be possible and often desirable. These can easily be made by the clinician using conventional monitoring techniques and dosimetric principles.

The present invention includes administration of one or a combination of cytokines, preferably lymphokines, prior to, together with and/or subsequent to administration of cytotoxic radioisotopes, drugs and/or toxins, alone or in combination, as such or in the form of antibody conjugates. The guidelines provided herein will enable the ordinary skilled clinician to adapt cytokine administration to enhance the efficacy and mitigate the adverse hematopoietic side effects of cytotoxic therapy as a function of WBC, platelet and erythrocyte counts, marrow component status and other particular diagnostic indicia peculiar to the individual patient. In general, this invention is applicable to support an enhancement of efficacy of any cytotoxic therapy that has serious hematopoietic side effects that limit the therapy's efficacy.

The present invention includes sterile injectable preparations and kits for use in practising the therapeutic methods described hereinabove. Cytotoxic radioisotopes, drugs and/or toxins and/or antibody conjugates thereof are normally administered as sterile injectable preparations. Where administration is to be intravenous or intraarterial, such solutions are normally prepared in sterile phosphate-buffered saline (PBS). Examples of solutions of radiolabeled antibody conjugates for anti-tumor therapy are given in the aforementioned Goldenberg patents. Similar solutions will be appropriate for intravenous or intraarterial infusions of cytotoxic drugs and/or toxins and/or antibody conjugates thereof. Where cytokine therapy is to be administered together with the cytoxic agent, the cytokine can be included in the solution of the agent for co-administration. Where, as is more often the case, administration of the cytokine is not simultaneous with that of the cytotoxic agent, a sterile solution of the cytokine in PBS will be appropriate, this mode being the preferred one to effect mitigation of bone marrow toxicity, even where administration of the cytotoxic agent is not intravenous or intraarterial. In cases where administration of the cytotoxic agent is intraperitoneal, intrathecal, subcutaneous or the like, conventional pharmaceutically acceptable sterile injection vehicles will be used for the adminstration of the agent. In cases where the cytokine treatment is an adjunct to organ transplantation, it will provided as a separate preparation.

Kits for therapy according to the present invention will normally include sterile preparations of the cytotoxic agent, either as solutions or as lyophilized solids ready for dissolution in the appropriate sterile injection medium, e.g., PBS. Such kits will include the appropriate dosage of cytokine, in cases where co-administration according to a predetermined protocol is envisioned. More often, particularly for adjunctive therapy of organ transplantation, the cytokine will be provided in a separate container, either in lyophilized form or as a sterile solution in, e.g., PBS, for administration in accordance with a protocol adapted to respond to the patient's hematological condition.

Without further elaboration, it is believed that one skilled in the art can, using the preceding description, utilize the present invention to the fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLES

1. Treatment of metastatic colon cancer with 5-FU+IL-1

A 62-year-old man presents with a colonic carcinoma metastatic to the liver, as shown by liver/spleen scan and CAT scan (about 6 cm in diameter), and having a plasma CEA level of 42 ng/ml. No other site of metastasis or recurrence has been found, and his general condition is very good (Karnovsky scale of 90). The patient is given 5-fluorouracil therapy over 5 days at a dose of 10 mg/kg intravenously, repeated every second day during the next five days, and then twice monthly (1st and 15th day of each month). In this type of therapy, toxicity usually begins to show by the 23rd day, whereby a drop in WBC's to less than 3,500/cmm is seen. In this case, after the second week of 5-FU therapy, the patient is infused on two alternate days with two doses of 10 ug IL-1 each. Upon measurement of the WBC's over the next two weeks, it is found that the usual drop is inhibited significantly, thus permitting the patient to receive more extensive 5-FU chemotherapy. IL-1 administration is repeated weekly or twice monthly, depending upon the patient's hematologic picture. As a result of this combination therapy, a 50% reduction in the liver metastasis is noted on CAT scan 5 months after onset of therapy.

2. Treatment of breast cancer with Adriamycin, Cytoxin, and IL-1.

A 55-year-old woman presents with clavicular and some rib metastases of a mammary carcinoma which has been resected 3 years earlier. She is given Adriamycin (30 mg/kg i.v. daily for 3 weeks) and Cytoxin (10 mg/kg i.v. every week). Two days prior to instituting this chemotherapy, she is given a slow infusion of 100 ug IL-1, and then one week later again at a dose of 50 ug. On day 10, only a marginal (less than 20%) drop in her WBC's occurs. Therefore, instead of subsequent courses of chemotherapy being reduced, as is conventionally practiced when hematologic side effects occur, a full course of both drugs is repeated under continued IL-1 therapy. Resolution of some of the rib metastases is seen radiologically 7 months later.

3. Treatment of colon cancer with Y-90-antibody conjugate and IL-1

A patient with peritoneal spread of a colon cancer which has been resected 2 years earlier and found to be a Dukes' C lesion, and having a CEA blood titer of 55 ng/ml, presents for experimental therapy, since previous chemotherapy trials with 5-FU have been unsuccessful. The patient is given a 35 mCi dose of Yttrium-90 conjugated to a F(ab')$_2$ fragment of a murine monoclonal antibody against carcinoembryonic antigen (CEA), by intraperitineal injection. Two days later, an infusion of 20 ug IL-1 is instituted i.v., and the patient's hematologic values monitored thereafter. No significant drop in WBC's is noted, thus permitting a repetition of the radioimmunotherapy 3 weeks later, followed again by IL-1 therapy. A third treatment is given 2 months later, and radiological evidence of some tumor and ascites reduction is noted 4 weeks later. Thus, the patient is able to tolerate higher and more frequent doses of the radioimmunotherapy agent.

4. Treatment of advanced ovarian cancer with P-32 and IL-1

A 60-year-old woman with advanced ovarian cancer, presenting with ascites and considerable distension of her abdomen, is given intraperitoneal P-32 therapy by injection of P-32-orthophosphate. After the first injection, an i.v. injection of 10 ug IL-1, repeated twice weekly, is instituted. The patient tolerates the P-32 therapy well, with only minimal hematologic toxicity noted. A minor response in her ovarian cancer is noted by radiological methods and by cytological analysis of the ascites fluid in her abdomen.

5. Treatment of cardiac transplant with Y-90-antibody conjugate and Il-1

A patient with end-stage myocardiopathy is to receive a heart transplant. At the day of surgery, the patient is infused i.v. with 20 mCi Y-90 conjugated to the monoclonal anti-Tac antibody of Uchiyama et al. referenced hereinabove, which binds to the human IL-2 receptor of activated T-lymphocytes. The patient is also given a dose of 20 ug IL-1 i.v., as well as conventional corticosteroid therapy. Ten days later, a second dose of 10 mCi Y-90-anti-Tac IgG is given i.v., but one day earlier, an i.v. injection of 20 ug IL-1 is also instituted. As of 10 weeks later, no evidence of graft rejection is noted, and the patient's hematologic picture is relatively normal. The only other immunosuppressive therapy given during this period is the oral application of corticosteroids. The patient's general condition is good.

6. Treatment of melanoma with I-131-antibody-IL-1 heteroconjugate

A 44-year-old male presents with multiple melanoma deposits in his skin, ranging from less than 1 cm on his chest to more than 3 cm in his axilla. The F(ab')$_2$ fragment of the 9.2.27 monoclonal antibody against human melanoma is conjugated to IL-1 by the aminodextran method of Shih et al., supra, whereby an average of 20 IL-1 molecules per aminodextran (15,000 dalton) and about 1 carrier per antibody fragment are loaded. The conjugate is then labeled with I-131 by the chloramine-T method, yielding a high specific activity of 15 mCi/mg antibody protein. The patient is then given a 6-hour i.v. infusion of the heteroconjugate, such that 70 mCi I-131 and 20 ug IL-1 are administered. One day prior to this and 4 days later, i.v. injections of 10 ug IL-1 are given. This therapy regimen is repeated 1 week later, and then again 4 weeks later. Hematological evaluation reveals a minor drop in WBC's (less than 20%), while evidence of disappearance of 2 small skin metastases and a 25–50% reduction of 3 larger melanoma sites is observed 2 months after onset of therapy.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a method of therapy of graft rejection, wherein a human patient undergoing a tissue or organ transplant is treated with a therapeutic amount of a cytotoxic agent which also produces hematopoietic or myeloid toxicity, the improvement which comprises administering to said patient an amount of a differentiation/maturation-inducing cytokine, prior to, simultaneously with or subsequent to exposure to said cytotoxic agent, wherein said amount is effective for substantially preventing, mitigating or reversing said hematopoietic or myeloid toxicity.

2. The method of claim 1, wherein said cytotoxic agent is selected from the group consisting of a radioisotope, drug, or toxin.

3. The method of claim 2, wherein said drug, toxin or radioisotope is conjugated to an antibody or antibody fragment.

4. The method of claim 3, wherein said antibody or antibody fragment specifically binds to an antigen which is produced by or associated with a lymphocyte.

5. The method of claim 1, wherein said cytokine is a lymphokine.

6. The method of claim 5, wherein said cytokine is interleukin-1 (IL-1).

7. The method of claim 1, wherein said cytokine is selected from the group consisting of a colony stimulating factor (CSF), interleukin-2 (IL-2), or interleukin-3 (IL-3).

8. The method of claim 2, wherein a radioisotope is administered.

9. The method of claim 3, wherein a radioisotope conjugate is administered.

10. The method of claim 2, wherein a drug or toxin is administered.

11. The method of claim 3, wherein a drug or toxin conjugate is administered.

12. The method of claim 2, wherein said cytokine is administered prior to or simultaneously with administration of said radioisotope, drug or toxin.

13. The method of claim 2, wherein said cytokine is administered subsequent to administration of said radioisotope, drug or toxin.

14. The method of claim 13, wherein said cytokine is administered at least 3 days after administration of said radioisotope, drug or toxin.

15. The method of claim 2, wherein said radioisotope, drug or toxin is administered by an intravenous or intraarterial route.

16. The method of claim 2, wherein said radioisotope, drug or toxin is administered by an intrathecal, intracavitary, intramuscular, subcutaneous or oral route.

17. The method of claim 3, wherein said radioisotope, drug or toxin conjugate is administered by an intravenous or intraarterial route.

18. The method of claim 3, wherein said radioisotope, drug or toxin is administered by an intrathecal, intracavitary, intramuscular, subcutaneous or oral route.

19. The method of claim 8, wherein said radioisotope is a beta-emitter.

20. The method of claim 8, wherein said radioisotope is an alpha-emitter.

21. The method of claim 1, wherein a combination of cytokines is administered.

22. The method of claim 4, wherein said cytotoxic agent is a cytotoxic drug conjugated to an antibody that specifically binds to lymphocytes.

23. The method of claim 4, wherein said antibody binds specifically to T-cells.

24. The method of claim 23, wherein said antibody binds specifically to the human IL-2 receptor.

25. The method of claim 1, wherein said cytotoxic agent is an unconjugated cytotoxic antibody.

26. The method of claim 21, wherein said combination of cytokines comprises more than one cytokine selected from the group consisting of interleukin-1 (IL-1), interleukin-2 (IL-2) interleukin-3 (IL-3), granulocyte macrophage-colony stimulating factor (GM-CSF), granulocyte-colony stimulating factor (G-CSF), macrophage-colony stimulating factor (M-CSF), or platelet growth factor.

27. The method of claim 26, wherein said combination of cytokines comprises interleukin-1 (IL-1) and one or more additional differentiation/maturation-inducing cytokines.

28. The method of claim 26, wherein said combination of cytokines comprises interleukin-1 (IL-1) and one or more additional differentiation/maturation-inducing cytokines other than interleukin-2.

29. The method of claim 27, wherein said one or more additional cytokines is interleukin-3 (IL-3).

30. The method of claim 24, wherein said antibody is an anti-Tac monoclonal antibody which specifically binds to the human IL-2 receptor of activated T-cells.

31. The method of claim 8, wherein said radioisotope is generated in situ by neutron irradiation of Boron-10 atoms.

* * * * *